US011883450B1

(12) United States Patent
Mohamed et al.

(10) Patent No.: US 11,883,450 B1
(45) Date of Patent: Jan. 30, 2024

(54) **EXTRACT OF *AGATHIS ROBUSTA* AS ANTIFUNGAL AGENT**

(71) Applicant: KING FAISAL UNIVERSITY, Al-Ahsa (SA)

(72) Inventors: Maged Elsayed Mohamed, Al-Ahsa (SA); Nancy Safwat Younis, Al-Ahsa (SA); Eman Fikry, Al-Ahsa (SA); Nora Tawfeek, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/141,357

(22) Filed: Apr. 28, 2023

(51) Int. Cl.
  *A61K 36/13* (2006.01)
  *A61K 47/28* (2006.01)
  *A61P 31/10* (2006.01)
  *A61K 9/00* (2006.01)
  *A61K 47/44* (2017.01)

(52) U.S. Cl.
  CPC ............ *A61K 36/13* (2013.01); *A61K 9/0014* (2013.01); *A61K 47/28* (2013.01); *A61K 47/44* (2013.01); *A61P 31/10* (2018.01)

(58) Field of Classification Search
  None
  See application file for complete search history.

(56) References Cited

U.S. PATENT DOCUMENTS

2002/0132021 A1* 9/2002 Raskin .................... A01H 3/00
                                                    424/773

FOREIGN PATENT DOCUMENTS

| WO | 2005012507 A1 | 2/2005 | |
|---|---|---|---|
| WO | 2006066355 A1 | 6/2006 | |
| WO | WO-2008119556 A2 * | 10/2008 | ............. A61K 35/60 |

OTHER PUBLICATIONS

Mohamed et al. ("Agathis robusta Bark Essential Oil Effectiveness against COVID-19: Chemical Composition, In Silico and In Vitro Approaches". Plants. 2022; 11(5):663) (Year: 2022).*
Marei et al. ("Comparative antifungal activities and biochemical effects of monoterpenes on plant pathogenic fungi", Pesticide Biochemistry and Physiology, vol. 103, Issue 1, 2012, pp. 56-61) (Year: 2012).*
Shilton, "The Effect of Plant Hormones on Phenolic Production in Kauri Trees", Auckland University of Technology (2017), thesis.
Frezza et al., "Phytochemistry, Chemotaxonomy, and Biological Activities of the Araucariaceae Family—A Review", Plants (2020) 9:888.
Mohamed et al., " Agathis robusta Bark Essential Oil Effectiveness Against Covid-19: Chemicl Composition, In Silico annd In Vitro Approaches", Plants (2022) 11:663.
Andjic et al., "Immortelle essential oil-based ointment improes wound healing in a diabetic rat model", Biomedicine and Pharmacotherapy (2022) 150:112941.

* cited by examiner

*Primary Examiner* — Robert A Wax
*Assistant Examiner* — Quanglong N Truong
(74) *Attorney, Agent, or Firm* — Nath, Goldberg & Meyer; Richard C. Litman

(57) ABSTRACT

The extract of *Agathis robusta* as an antifungal agent is prepared by hydrodistillation of the powdered bark of *A. robusta* in a Clevenger-type apparatus at 100° C. for 6 hours to obtain the essential oils of *A. robusta*. The essential oil is mixed with an ointment base of cholesterol, liquid paraffin, lanolin, and vaseline album, the powdered essential oil of *A. robusta* being added to the ointment base at 1 or 2% w/w and homogenized to a smooth ointment. When tested in vivo on Wistar rats topically infected with *Candida albicans*, both the 1% and 2% ointment formulations demonstrated substantial antifungal activity.

5 Claims, 7 Drawing Sheets

EXTRACT OF *AGATHIS ROBUSTA* AS ANTIFUNGAL AGENT

BACKGROUND

1. Field

The disclosure of the present patent application relates to topical antifungal agents, and particularly to an extract of *Agathis robusta* as an antifungal agent, the extract including essential oils of *A. robusta*.

2. Description of the Related Art

The tree *Agathis robusta*, commonly known as Queensland Kauri, is native to New Guinea and Queensland, Australia. A coniferous tree, *A. robusta* is sometimes called a pine tree, but it is not a true pine, bearing leaves instead of needles on its branches. The tree produces high-quality timber. Although a few medicaments have been produced from *A. robusta*, its use for treatment of fungal skin infections has not been previously reported.

Dermatomycoses is a medical term encompassing various types of fungal skin infection, including the various forms of linea and candidiasis. Treatment is usually by administration of pharmaceuticals, which may be delivered orally, intravenously or by topical application, depending on the location and severity of the infection. While such treatment is often effective to at least some degree, the prevalence and different presentations of such fungal skin infections renders the development of new active ingredients and new formulations for the treatment of dermatomycoses desirable. Thus, an extract of *Agathis robusta* as an antifungal agent solving the aforementioned problems is desired.

SUMMARY

The extract of *Agathis robusta* as an antifungal agent is prepared by hydrodistillation of the powdered bark of *A. robusta* in a Clevenger-type apparatus at 100° C. for 6 hours to obtain the essential oils of *A. robusta*. The essential oil is mixed with an ointment base of cholesterol, liquid paraffin, lanolin, and vaseline album, the essential oil of *A. robusta* being added to the ointment base at 1 or 2% w/w and homogenized to a smooth ointment. When tested in vivo on Wistar rats infected with *Candida albicans*, both the 1% and 2% ointment formulations demonstrated substantial antifungal activity.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
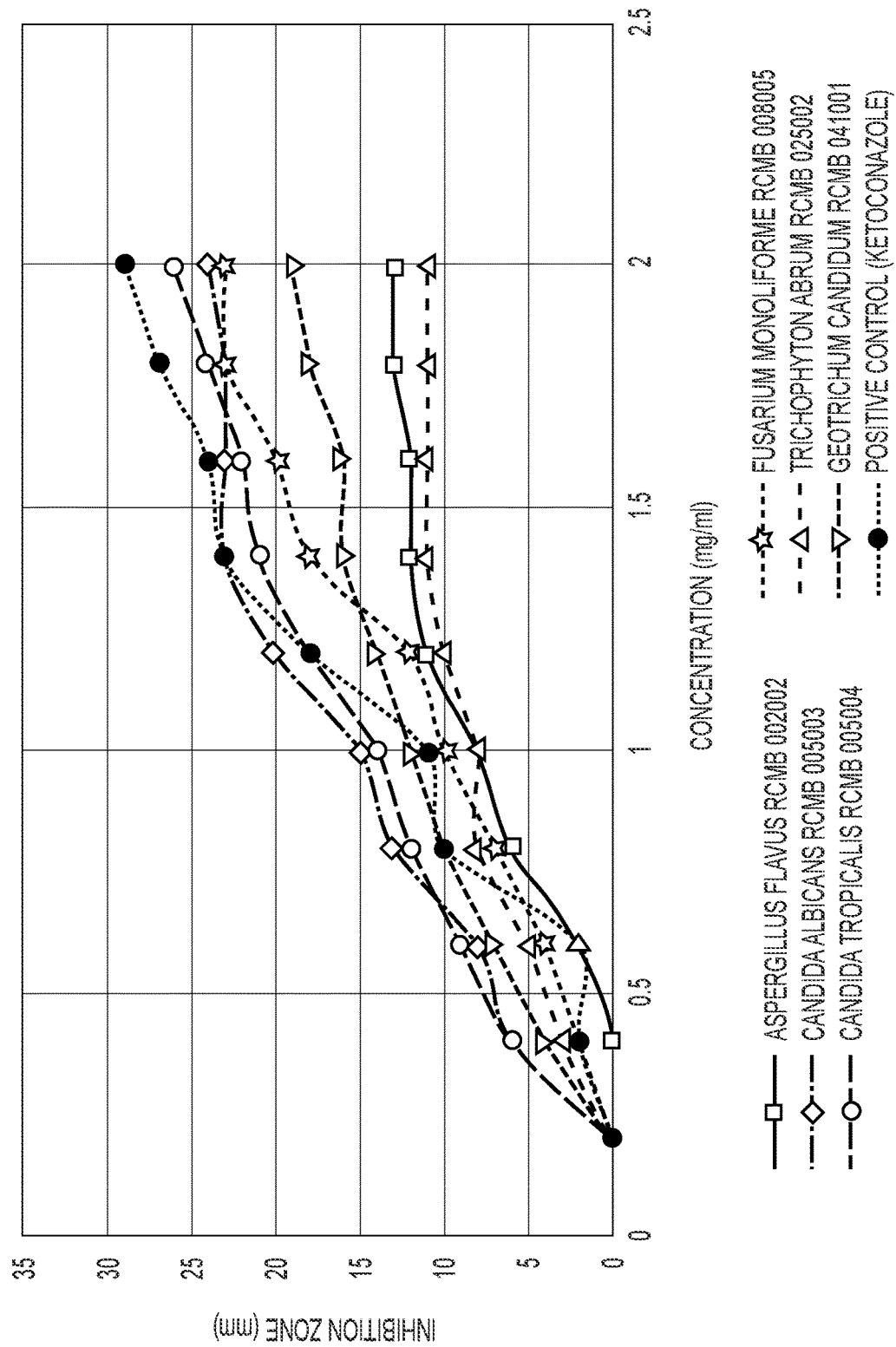
FIG. 1A is a composite plot of the inhibition zone for various fungi.

The extract of *Agathis robusta* as an antifungal agent is prepared by hydrodistillation of the powdered bark of *A. robusta* in a Clevenger-type apparatus at 100° C. for 6 hours to obtain the essential oils of *A. robusta*. The essential oil is mixed with an ointment base of cholesterol, liquid paraffin, lanolin, and vaseline album, the essential oil of *A. robusta* being added to the ointment base at 1 or 2% w/w and homogenized to a smooth ointment. When tested in vivo on Wistar rats infected with *Candida albicans*, both the 1% and 2% ointment formulations demonstrated substantial antifungal activity.

The extract of *Agathis robusta* as an antifungal agent will be better understood by reference to the following examples.

For the following examples, the fresh bark of the cultivated tree of *Agathis robusta* was collected at the cone maturation stage from El-Orman Botanical Garden, Giza, Egypt (July 2021). Dr Therese Labib, Consultant of Plant Taxonomy at the Ministry of Agriculture and the Former Director of Orman Botanical Garden, Giza, Egypt, had kindly confirmed the identity of the plant.

The fungal stains used in testing for minimum fungicidal concentration (MFC) were *Aspergillus flavus* RCMB 002002, *Candida albicans* RCMB 005003, *Candida tropicalis* RCMB 005004, *Fusarium moniliforme* RCMB 008005, *Trichophyton rubrum* RCMB 025002, and *Geotrichum candidum* RCMB 041001. However, only *Candida albicans* RCMB 005003 was used in in vivo experiments.

Example 1

Extraction of *A. robusta* Essential Oils

The *Agathis robusta* essential oil was prepared as described in Mohamed, et al., "*Agathis robusta* Bark Essential Oil Effectiveness against COVID-19: Chemical Composition, In Silico and In Vitro Approaches", Plants (2022), 11(5):663. In brief, the shade-dried bark of *A. robusta* (300 g) was pulverized into a coarse powder, soaked in 300 ml of distilled water (for 24 hours), and then subjected to hydrodistillation using the Clevenger-type apparatus. Hydro-distillation was performed under atmospheric pressure at 100° C. for 6 h. The recovered volatile fraction was dried by mixing with anhydrous sodium sulfate, and the obtained essential oil samples were retained in brown vials in the refrigerator (4° C.) until used.

Example 2

Determination of the Antifungal Activity of *A. robusta* Bark Essential Oil

The fungi strains were grown at 27° C. for 48 h in Sabouraud dextrose broth. The growth of the fungal strains was adjusted to OD600 of 0.1, and then 100 µL of the fungi-containing broth was spread on solid Sabouraud dextrose broth Petri dishes. *A. robusta* bark essential oil was used to impregnate 7 mm filter paper disks with concentrations 0.2, 0.4, 0.6, 0.8, 1.0, 1.2, 1.4, 1.6, 1.8, and 2.0 mg/mL essential oil in DMSO per filter paper disk. Negative and positive controls were implemented by impregnating 7 mm diameter filter paper with DMSO and Ketoconazole control, respectively. The Petri dishes were incubated at 27° C. for 72 h, and the antifungal activity was assessed through the analysis of the inhibition zone diameter. Every concentration was repeated 5 times in three different experiments, and the mean and SD of inhibition zones were calculated for each fungal strain.

The results identified that the oil was active against all fungal stains tested in concentrations ranging from 0.7 to 2 mg/mL. The oil demonstrated the maximum antifungal activity against *Candida albicans* RCMB 005003 (maximum inhibition zone diameter of 2.4 cm), and *Candida tropicalis* RCMB 005004 (maximum inhibition zone diameter of 2.6 cm), (see FIG. 1A), representing 82% and 89%, respectively, of the inhibition zone of the positive control (ketoconazole). The oil showed the lowest activity against *Trichophyton rubrum* RCMB 025002 and *Aspergillus flavus* RCMB 002002, showing 38% and 45% of the inhibition zone of the positive control (ketoconazole), (see FIG. 1A). The oil showed a more rapid onset for the antifungal activity than the positive control (ketoconazole) with the majority of the fungal strains, (see FIG. 1A).

Figure 1B:
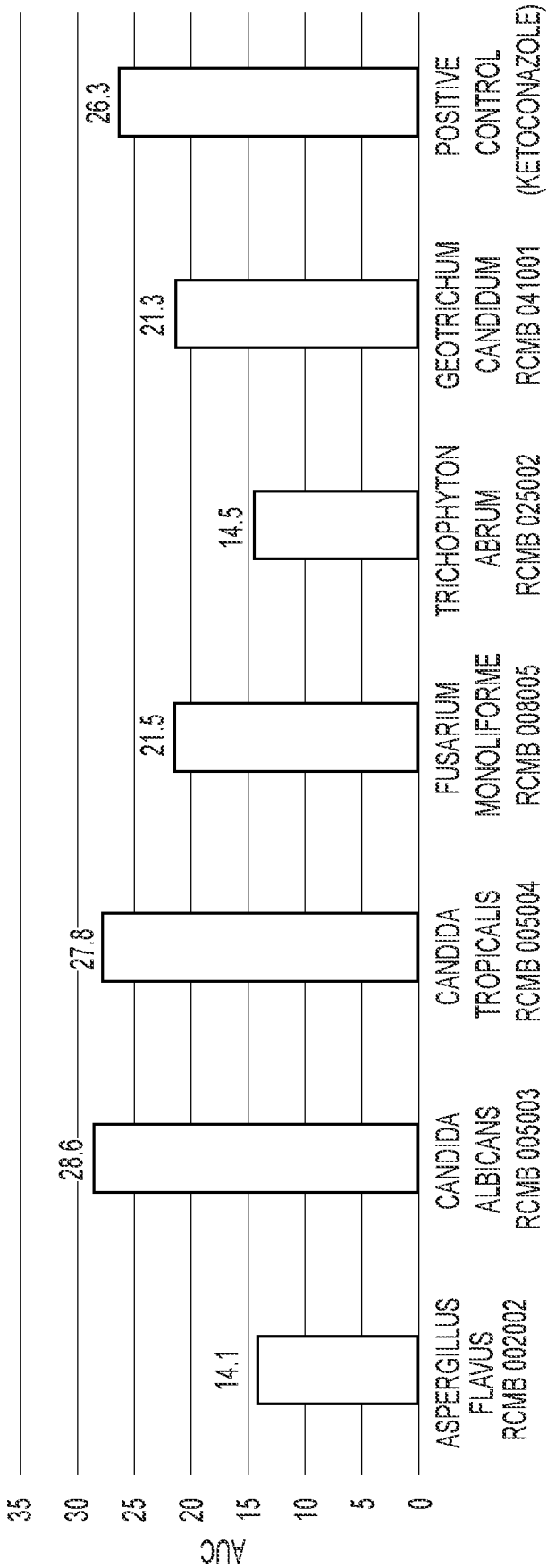
FIG. 1B is a chart of the area under the curves in FIG. 1A for various fungi

When the area under the curve (AUC), FIG. 1B, is considered, the oil demonstrated better AUC against *Candida albicans* RCMB 005003 and *Candida tropicalis* RCMB 005004 than the positive control (ketoconazole), representing 108% and 106%, respectively.

Example 3

Minimum Fungicidal Concentration (MFC) of *A. robusta* Bark Essential Oil

Minimum fungicidal concentration (MFC) was determined according to Zinsou et al., "Development of new dermatological formulations for the treatment of cutaneous candidiasis", Scientific African (2020), 8:e00342. Different final concentrations (0.1 to 1 mg/mL) of the bark essential oils were dissolved in DEMO and added to liquid Sabouraud dextrose broth. From the above fungal stain suspension, 1 mL was added to each essential oil tube. The tubes were incubated at room temperature for three days. Negative and positive controls were made through the addition of an equivalent amount of DMSO and Ketoconazole, respectively. MFC was calculated through the determination of the lowest concentration of the essential oil, which could inhibit the growth of the fungus. Every concentration was repeated 5 times in three different experiments, and the mean and SD of inhibition zones were calculated for each fungal strain. The MIC was determined as the lowest concentration of essential oil that inhibited fungal growth after 48 h.

The MIC was determined for the *A. robusta* bark essential oil and the results are stated in Table 1.

TABLE 1

| MIC for *A. robusta* bark essential oil | |
| --- | --- |
| Fungi stains | Essential oil MFC (µg/mL) |
| Negative Control (DMSO) | 0 |
| *Aspergillus flavus* RCMB 002002 | 2.4 |
| *Candida albicans* RCMB 005003 | 0.4 |
| *Candida tropicalis* RCMB 005004 | 0.75 |
| *Fusarium moniliforme* RCMB 008005 | 0.82 |

TABLE 1-continued

| MIC for *A. robusta* bark essential oil | |
| --- | --- |
| Fungi stains | Essential oil MFC (µg/mL) |
| *Trichophyton rubrum* RCMB 025002 | 1.94 |
| *Geotrichum candidum* RCMB 041001 | 1.2 |
| Positive Control (Ketoconazole) | 0.037 |

In accordance with the antifungal activity experiment, the *A. robusta* bark essential oil exhibited low MFC against *Candida* species, followed by the oil effect on *Fusarium moniliforme*. The oil showed a lesser fungicidal effect on *Trichophyton rubrum*, *Geotrichum candidum* and *Aspergillus flavus*.

Both the MFC and the antifungal experiment allowed the identification of the 1% and 2% oil concentrations for use in the antifungal topical preparation. Both in vitro experiments recommended the use of *Candida albicans* as the microbial infection agent.

Example 4

Preparation of Topical Formulation of *A. robusta* Essential Oil Ointment

The *Agathis robusta* essential oil (1% and 2%) was put into a simple ointment base according to Andjid et al., "Immortelle essential oil-based ointment improves wound healing in a diabetic rat model", Biomedicine & Pharmacotherapy (2022), 150:112941 using the following ingredients: 5% Cholesterol (5 g/100 gm), 15% Liquid paraffin (15 g/100 gm), 15% Lanolin (15 g/100 gm), and 65% Vaseline album (65 g/100 gm). All the components were mixed to form the simple ointment base. The prepared *Agathis robusta* essential oil (from Example 1, above) was added at a concentration of 1% or 2% (w/w) (i.e., 1 or 2 gm/100 gm) of the ointment and gently mixed in a homogenizer, resulting in a smooth formulation.

Example 5

The Development of In Vivo Topical Fungal Infection

The development of in vivo topical fungal infection was determined according to Zinsou, A. et al., "Development of new dermatological formulations for the treatment of cutaneous candidiasis", Scientific African (2020):8:e00342, and modified Ray and Wuepper, "Experimental Cutaneous Candidiasis in Rodents: II. Role of the Stratum Corneum Barrier and Serum Complement as a Mediator of a Protective Inflammatory Response", Archives of Dermatology (1978), Vol. 114(4): 539-43. The experimental protocol was permitted by the Institutional Animal Care and Use Committee of King Faisal University (KFU-REC-2023-JAN-EA000691). All the experiments were executed in harmony with the relevant procedures and regulations of the Ethical Conduct for the Use of Animals in Research at King Faisal University. Wistar rats weighing (220±30 g) were used for the whole experiment. The animals' backs were shaved after anesthesia, and sterilized with 70% ethyl alcohol in water and left to dry. The injury was induced on the shaven back of each rat using a hot copper metal rod. The injury was swabbed with 0.5 mL broth containing 108 Colony-Forming Units (CFU) of *C. albicans*. The essential oil topical preparations were applied once daily, starting from day 3, directly on the infected wound until the wound was completely healed (nearly 20 days). No antibiotic or antifungal preparations were administered to any of the animal groups, and the animals were monitored daily for any wound contamination. The animals' wounds were covered by sterile wound plaster, which is changed every day.

The animals were divided into 5 groups: Group 1, "Infected", rats with injury and infected with *C. albicans* but without treatment (only the basic ointment without the essential oil); Group 2, "Infected+1% ARBEO", rats with injury, infected with *C. albicans* and treated with 1% *A. robusta* bark essential oil (ARBEO) ointment; Group 3, "Infected+2% ARBEO" rats with injury, infected with *C. albicans* treated with 2% *A. robusta* bark essential oil (ARBEO) ointment; and Group 4, "Infected+Keto", rats with injury, infected with *C. albicans* and treated with ketoconazole cream as a positive control.

The animals' infected wounds (lesions) were monitored according to Masoko, et al., "In vivo antifungal effect of Combretum and Terminalia species extracts on cutaneous wound healing in immunosuppressed rats", Pharm Biol (2010): 48:6:621-32, and Sullivan, et al., "Assessment of wound bioburden development in a rat acute wound model: Quantitative swab versus tissue biopsy", Wounds (2004): 16: 115-123, using the following parameters: (1) Presence and type of exudate, erythema, swelling, ulceration, and crust formation: The scoring of the lesions regarding the exudate was measured using the following criteria: 0: No exudate, 1: Exudate just visible, 2: Exudate easily visible, 3: Substantial quantity of exudate, 4: Large quantity of exudate; (2) Wound contraction percentage: The lesion diameters were determined in millimeters (mm) vertically and horizontally. The lesion size percentage was calculated using the below equation:

Wound contraction percentage=((Wound area day 0-Wound area day $X$)/Wound area day 0)×100, where $X$ represents the number of days;

(3) Epithelialization time: The number of days needed for the wound Escher to fade away, leaving no visible wound, was used to determine the epithelialization period. (4) Evaluation of wound fungal load was determined according to Sullivan et al., supra: At the $3^{rd}$, 10th, and 15 days, each lesion was gently swabbed by a sterile swab 3 times anti-clockwise with mild pressure. Each swab was placed into a sterile saline tube (2 mL), followed by serial dilution (5 times) using 1 mL of the swabbed saline and 1 mil of fresh sterile saline. Finally, 100 μl of the final dilution was spread into yeast malt agar plates to allow separated colonies formation. The plates were incubated for 48 hours at 37° C., and the number of yeasts on each plate was manually counted. The percentage of fungicidal activity was determined using the following formula:

The percentage of fungicidal activity=((Number of fungus colonies in day 0-Number of fungus colonies in day $X$)/Number of fungus colonies in day 0)×100, where X represents the number of days.

The in vivo wound infection results demonstrated the effect of the essential oil preparation of *A. robusta* on the wound exudate, wound contraction percentage, epithelization, and the percentage inhibition of wound fungal infection. As demonstrated in FIGS. 2A, 2B, 3, 4, and 5.

Figure 2A:
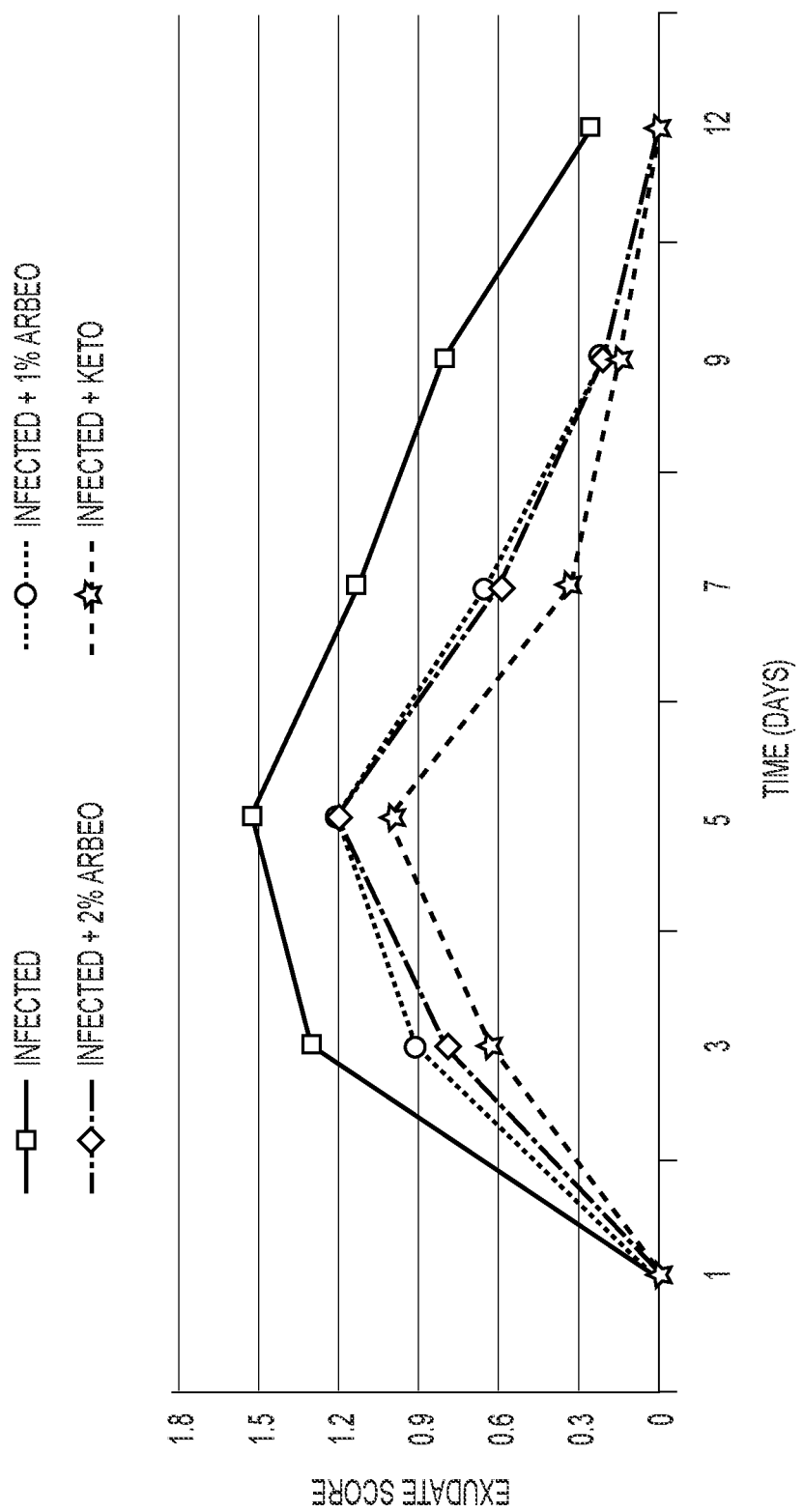
FIG. 2A is a plot of exudate wound scores for *C. albicans* and the effect of the essential oil of *A. robusta*.
Figure 2B:
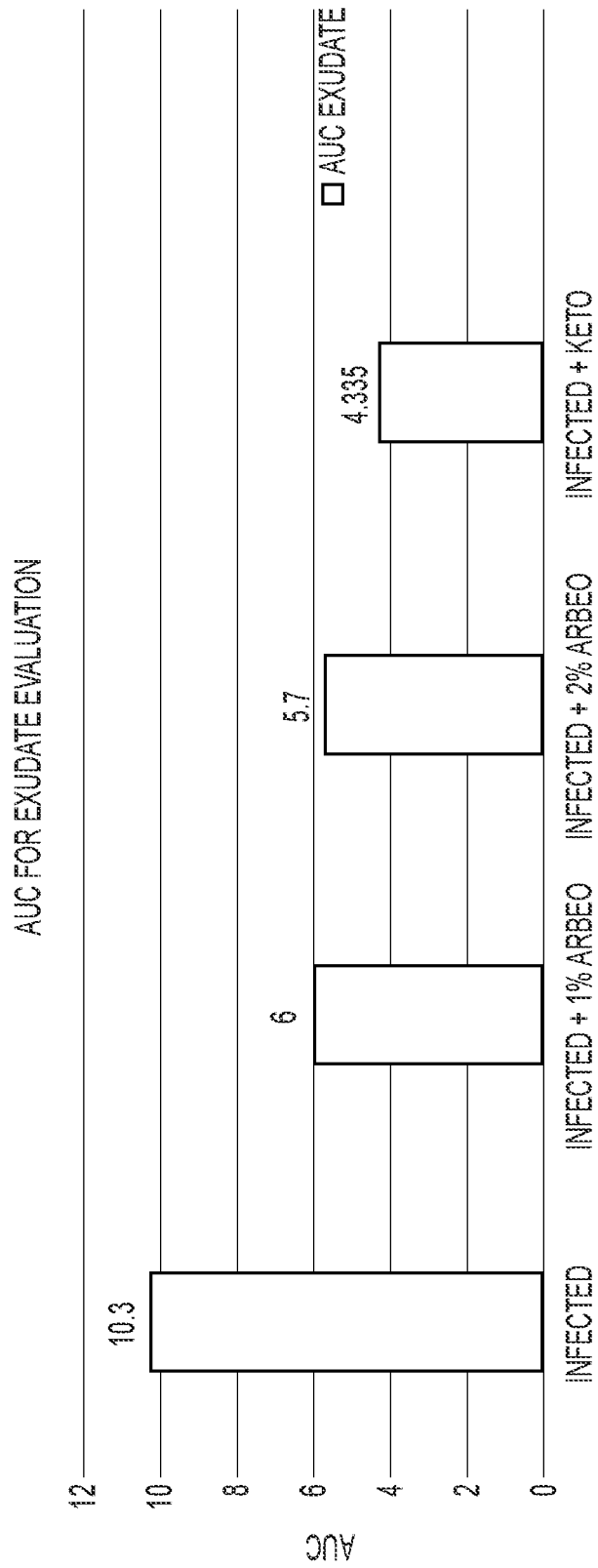
FIG. 2B is a chart of the area under the curve in FIG. 2A for various concentrations of essential oil of *A. robusta*.

FIG. 2A demonstrates the scoring of wound exudate on different days of the experiment. The exudate discharge starts to increase on day 3 and reaches the maximum on day 5, then reduces to nearly finished on day 12. The same pattern is followed after the application of *A. robusta* bark essential oil or ketoconazole (positive control). However, the amount of exudate is less in the oil case and much less with ketoconazole. The administration of 1% and 2% oil formula to the wound reduced the exudate by 41% and 44.6%, respectively, when related to the non-treatment lesions. However, ketoconazole reduced the exudate by 58% when related to the non-treatment lesions, FIG. 2B.

Figure 3:
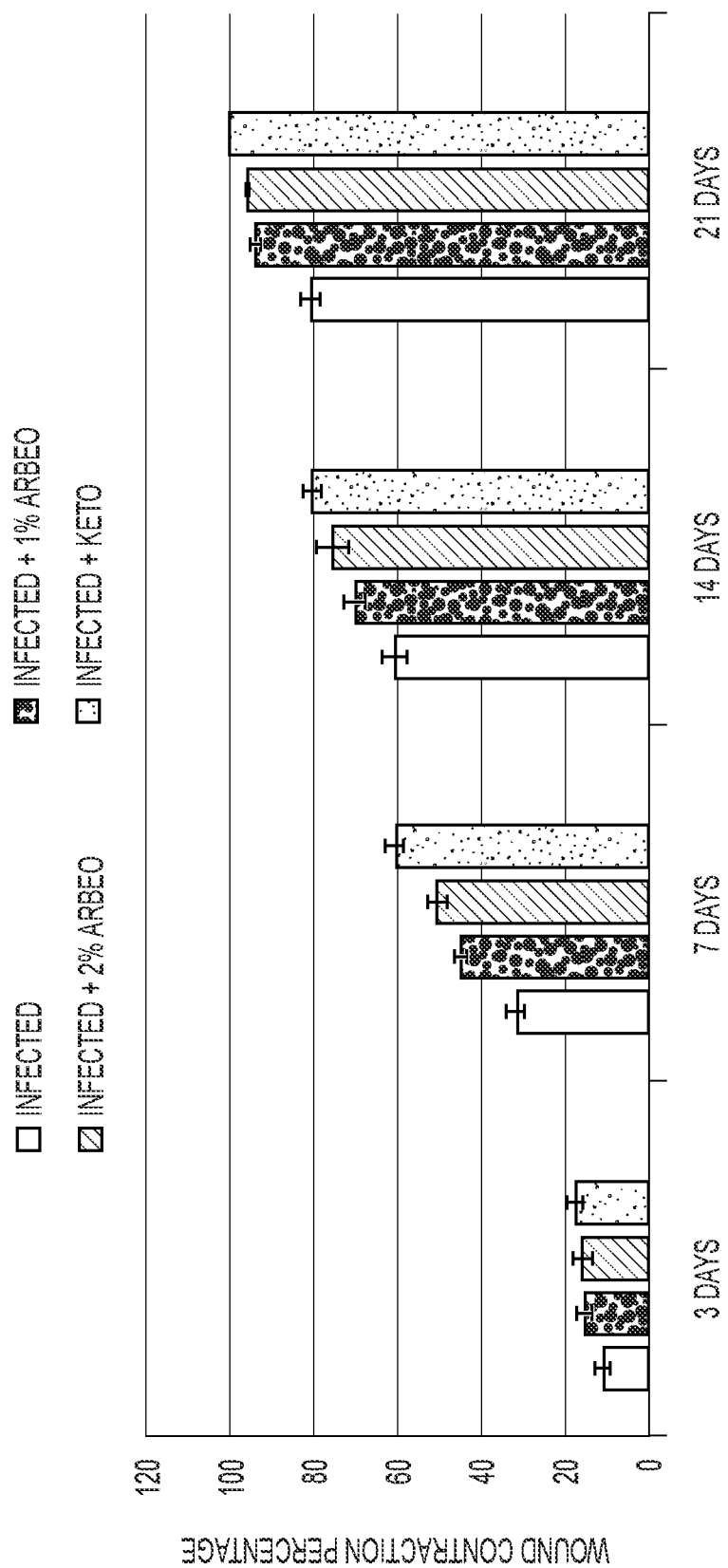
FIG. 3 is a chart of wound contraction percentage for *C. albicans* as function of days.

FIG. 3 shows the wound contraction percentage of the infected wounds. As time (days) passes, the wound contraction percentage increase to reach 80% and 100% by day 21 with negative and positive controls, respectively. The application of the essential oil increased the wound contraction rate to 94% and 96% for the 1% and 2% oil formulas, respectively. This represents a 17.5% and 20% increase in wound contraction rate to untreated wounds.

Figure 4:
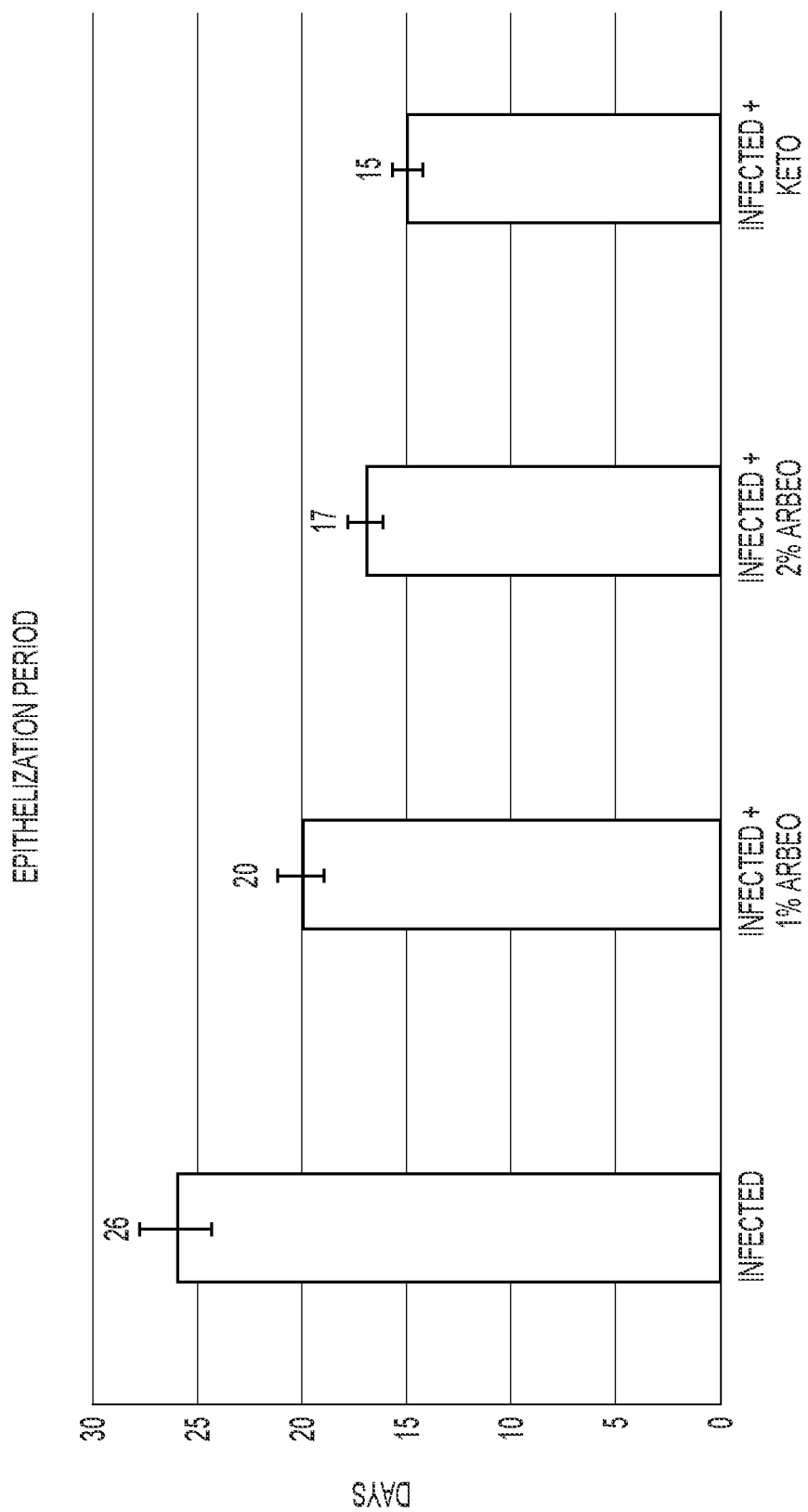
FIG. 4 is a chart of the epithelization period of wounds infected with *C. albicans* as affected by a topical composition including the essential oils o *A. robusta*.

The epithelization time of the infected wounds was calculated and represented in FIG. 4. The application of Ketoconazole (positive control) reduced the time required for wound epithelization by 42% when related to the untreated infected wound. Similarly, the application of 1% and 2% *A. robusta* bark essential oil formula reduced the epithelization time by 23% and 34.6% when related to the untreated infected wound.

Figure 5:
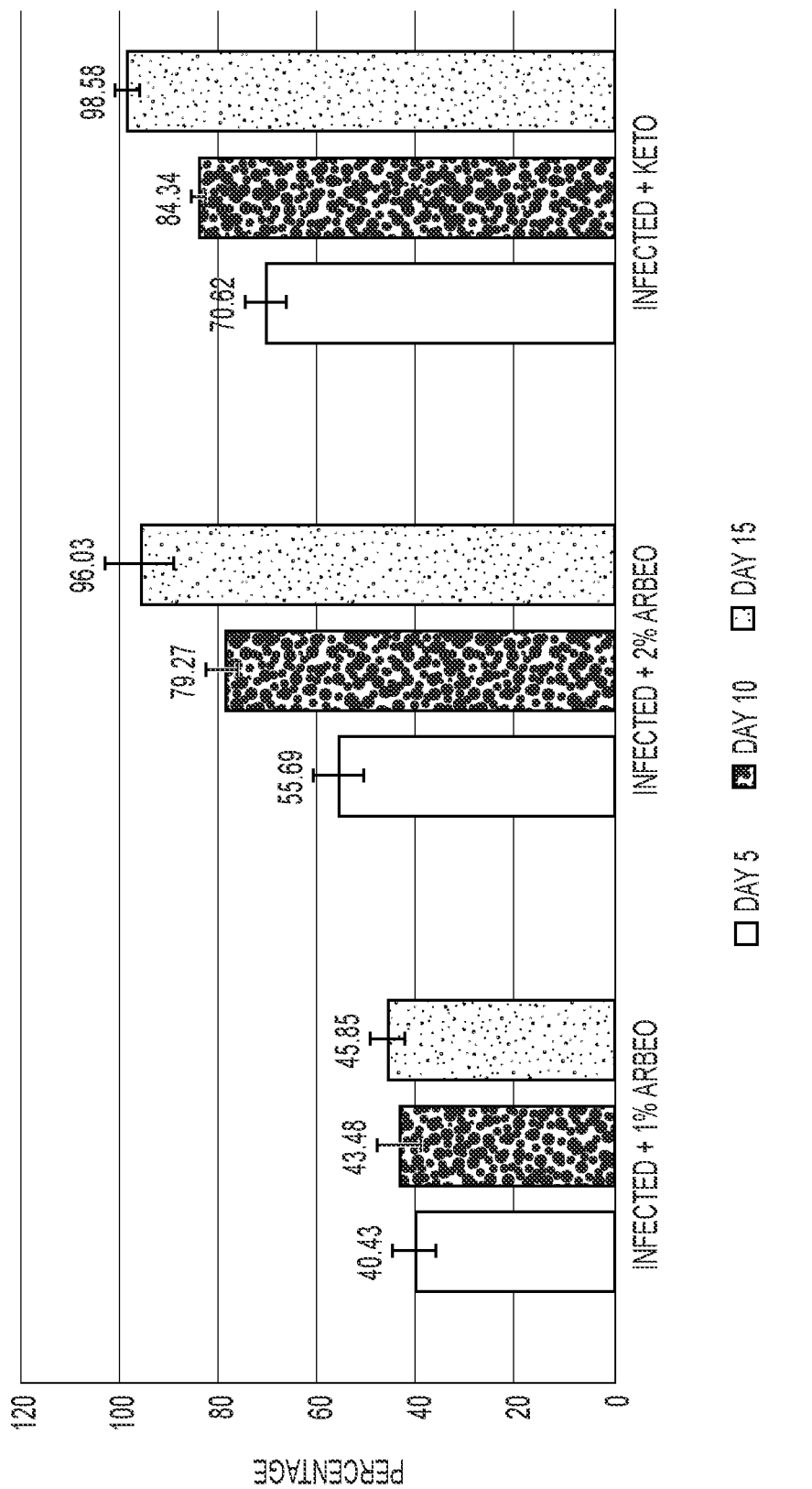
FIG. 5 is a chart showing inhibition of wounds infected with *C. albicans* and the effect of the topical composition including the essential oils of *A. robusta*.

FIG. 5 demonstrates the fungal load of infected wounds per time, as measured in days 5, 10 and 15, by calculating the number of fungal colonies extracted from infected wounds for the treated and positive control relative to the untreated (negative control). On day 5, the percentage of fungicidal activity of 1%, 2% and positive control reached 40.43%, 43.48%, to 45.85%, respectively, when related to the untreated-infected wound. This percentage increased to 70.62%, 84.34% and 98.58%, respectively, on day 15, indicating the fungicidal activity of the essential oil-containing formula and the positive control.

It is to be understood that the extract of *Agathis robusta* as an antifungal agent is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating a fungal infection of skin, comprising topically applying an antifungal agent to the fungal infection; wherein the antifungal agent comprises:
    essential oils extracted from bark of *Agathis robusta*; and
    an ointment base, the essential oils extracted from the bark of *Agathis robusta* being mixed with the ointment base to form a homogenized ointment adapted for topical application for treatment of dermatomycoses, the essential oils extracted from the bark of *Agathis robusta* being between 1% w/w and 2% w/w of the homogenized ointment.

2. The method of treating a fungal infection of skin according to claim 1, wherein the fungal infection is a result of infection by *Candida albicans*.

3. The method of treating a fungal infection of skin according to claim 1, wherein the essential oils extracted from the bark of *Agathis robusta* is 1% w/w of the homogenized ointment.

4. The method of treating a fungal infection of skin according to claim 1, wherein the essential oils extracted from the bark of *Agathis robusta* is 2% w/w of the homogenized ointment.

5. The method of treating a fungal infection of skin according to claim 1, wherein said ointment base comprises a mixture of cholesterol, liquid paraffin, lanolin, and petroleum jelly.

\* \* \* \* \*